(12) United States Patent  (10) Patent No.: US 8,192,403 B1
Pursley  (45) Date of Patent: Jun. 5, 2012

(54) SIDE PORT CATHETER DEVICE AND METHOD FOR ACCESSING SIDE BRANCH OCCLUSIONS

(75) Inventor: Matt D. Pursley, Alpharetta, GA (US)

(73) Assignee: Volcano Corporation, Rancho Cordova, CA (US)

( * ) Notice: Subject to any disclaimer, the term of this patent is extended or adjusted under 35 U.S.C. 154(b) by 0 days.

(21) Appl. No.: 12/890,353

(22) Filed: Sep. 24, 2010

Related U.S. Application Data

(62) Division of application No. 11/838,297, filed on Aug. 14, 2007.

(60) Provisional application No. 60/837,900, filed on Aug. 14, 2006.

(51) Int. Cl.
*A61M 5/178* (2006.01)
*A61M 25/00* (2006.01)
*A61B 5/00* (2006.01)

(52) U.S. Cl. .................... 604/164.13; 600/585

(58) Field of Classification Search ............ 604/523, 604/528, 510, 500, 164.01–164.13, 264; 600/114–115, 585; 128/898
See application file for complete search history.

(56) References Cited

U.S. PATENT DOCUMENTS

| | | | | |
|---|---|---|---|---|
| 5,366,490 A | * | 11/1994 | Edwards et al. | 607/99 |
| 6,599,316 B2 | * | 7/2003 | Vardi et al. | 623/1.15 |
| 2004/0039371 A1 | * | 2/2004 | Tockman et al. | 604/528 |
| 2009/0259288 A1 | * | 10/2009 | Wijay et al. | 623/1.11 |

* cited by examiner

*Primary Examiner* — Matthew F Desanto
(74) *Attorney, Agent, or Firm* — Jeffrey L. Thompson; Thompson & Thompson, P.A.

(57) ABSTRACT

A medical device and method are provided for accessing a side branch in an artery. The device includes a catheter having a sidewall, an internal lumen, and a side port formed through the sidewall. A perforating guide wire has a proximal portion within the internal lumen and a distal portion arranged to be movable out of the side port. The guide wire can be delivered through the side port to a side branch artery when the catheter is deployed to a location with the side port aligned with the side branch artery. In another embodiment, the catheter has inner and outer telescoping tubes with offset exit ports formed therein. The telescoping tubes can be used to change the degree of deflection of the perforating guide wire by changing the relative positions of the offset exit ports.

4 Claims, 9 Drawing Sheets

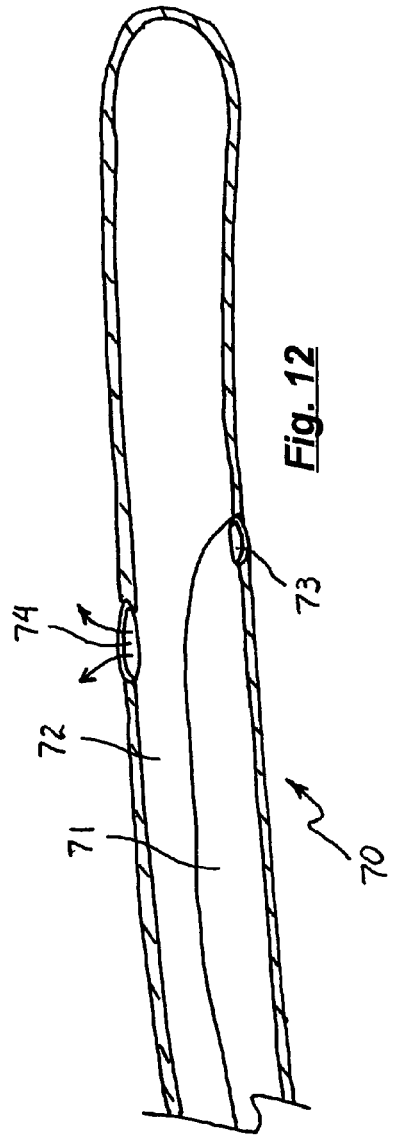
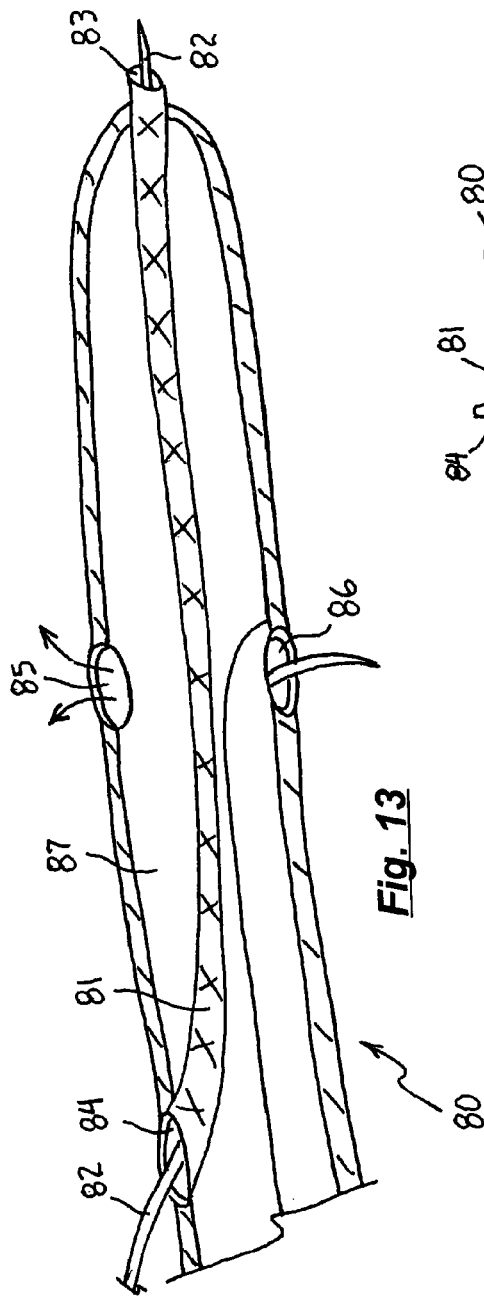
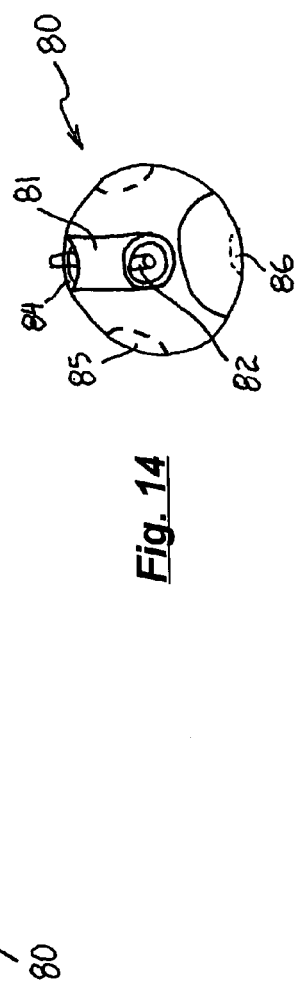

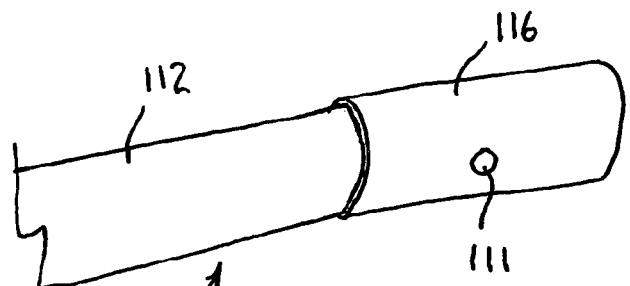
*Fig. 19*
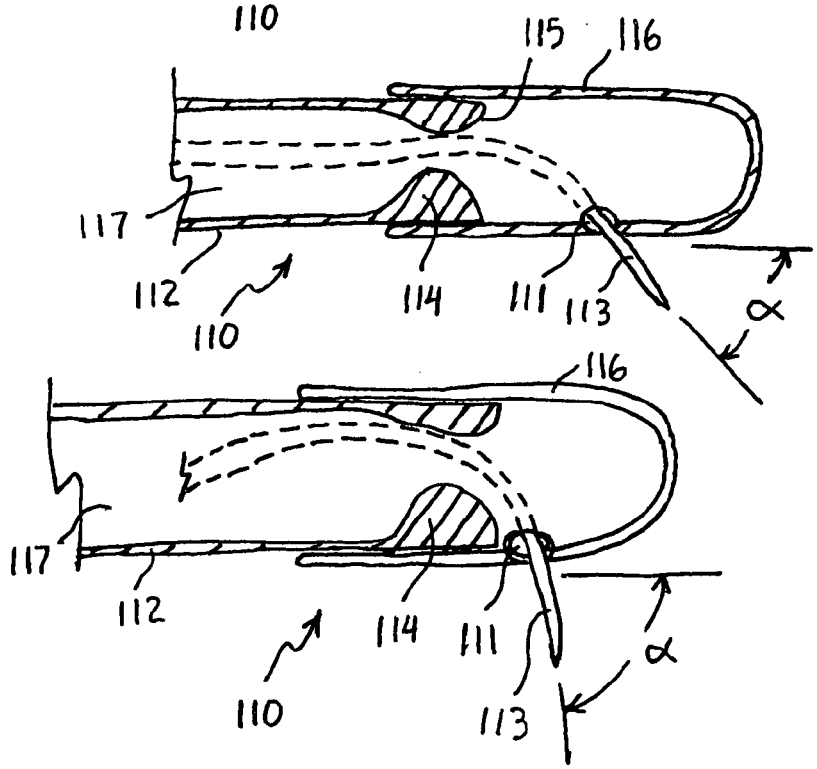
*Fig. 20*
*Fig. 21*
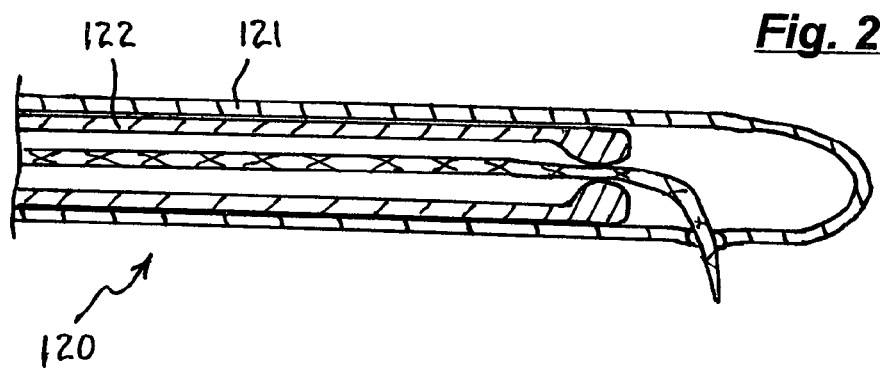
*Fig. 22*

SIDE PORT CATHETER DEVICE AND METHOD FOR ACCESSING SIDE BRANCH OCCLUSIONS

RELATED APPLICATIONS

This application is a divisional of U.S. patent application Ser. No. 11/838,297 filed on Aug. 14, 2007, and claims priority of U.S. Provisional Application No. 60/837,900 filed on Aug. 14, 2006. The content of these prior applications are incorporated herein by reference.

BACKGROUND OF THE INVENTION

1. Field of the Invention

The present invention relates generally to catheters and methods of treating the stenosis of an artery. In particular, the present invention relates to catheters and methods for accessing chronic total occlusions (CTOs) in arteries caused by the buildup of arterial plaque tissue.

2. Description of the Related Art

Chronic total occlusion (CTO) is a condition where arterial plaque tissue grows to complete stenosis of an artery and prohibits blood flow. A CTO is formed by the agglomeration of three separate physiological materials: (i) cholesterol or fat, (ii) collagen or fibrous matter, and (iii) calcium-based deposits. A CTO is also often referred to as a functional occlusion.

There are two causal pathogenic phenomena often associated with the formation of a CTO. The first is the late development of an acute occlusion. The second is the progressive occlusion of a long-term high degree stenosis. Both involve a pre-existing plaque or thrombus to which the fat and fibrous material adhere, building up until a blockage of the blood vessel occurs. A CTO 10 will sometimes form in a side branch 11 of an artery 12 as shown in FIG. 1, which is difficult to access using conventional catheters and surgical techniques.

Physicians currently attempt to perforate CTOs 10 in side branches 11 using a stiff guide wire 13 as shown in FIG. 2. A small catheter 14 is used to position the guide wire 13 at the occlusion 10.

Another conventional technique involves the use of a curved catheter 15 to align a perforating guide wire 16 with the angle of the side branch 11, as shown in FIG. 3. One of the primary problems with this approach occurs when a compressive force is applied to the guide wire 16. The guide wire 16 must be pushed to perforate the occlusion 10 and as it is pushed, the catheter 15 in which the guide wire 16 is contained reacts in a negative manner, as shown in FIG. 4. As can be seen, the catheter 15 will be pushed and/or rotated away from the side branch 11, or misaligned with the side branch 11, as compressive force is exerted on the guide wire 16. The restraint offered by the catheter 15 is limited because it must be made of a material that is soft enough not to injure the arteries as it is advanced into the vascular system. Catheters are limited as to the amount of stiffness the catheter can contain before it will injure the artery as it is aligned with the side branch. In addition, the curvature of the catheter can cause substantial "whip" as a physician torques the catheter to align it with the side branch.

A compliant balloon 17 can be attached to the catheter 18 to help limit the reaction forces on the catheter 18, as shown in FIG. 5. The balloon 17 is inflated through a separate lumen in the catheter 18. The balloon 17 allows for more stability in the catheter 18 as it is used. However, it still suffers from the cantilever type positioning exhibited in FIG. 4. In addition, it is still subject to whip caused by the curvature of the catheter as torque is applied to position the catheter.

There is a need in the industry for improved devices and methods to assist surgeons in accessing CTOs in side branches of arteries.

BRIEF DESCRIPTION OF THE DRAWINGS

The present invention will become more clearly appreciated as the disclosure of the present invention is made with reference to the accompanying drawings. In the drawings:

FIG. 12 shows another embodiment of the present invention in which two lumens are provided in the catheter; one lumen leading to the side port and the other lumen providing a passage for inflating support balloons attached to the catheter.

FIGS. 13 and 14 are side and end views of another embodiment of the present invention in which a channel is provided for inserting the catheter over a guide wire previously placed in the non-occluded artery.

FIGS. 19 to 21 show another embodiment of the present invention in which the side port is movable relative to the base catheter to change the angle at which the guide wire exits the catheter.

FIG. 22 shows another embodiment of the present invention in which telescoping sleeves are used to change the angle at which the guide wire exits the catheter.

DETAILED DESCRIPTION OF THE INVENTION

Side port catheters and methods for accessing side branch occlusions in arteries according to the present invention will now be explained in detail with reference to FIGS. 6 to 22 of the accompanying drawings.

Figure 1:
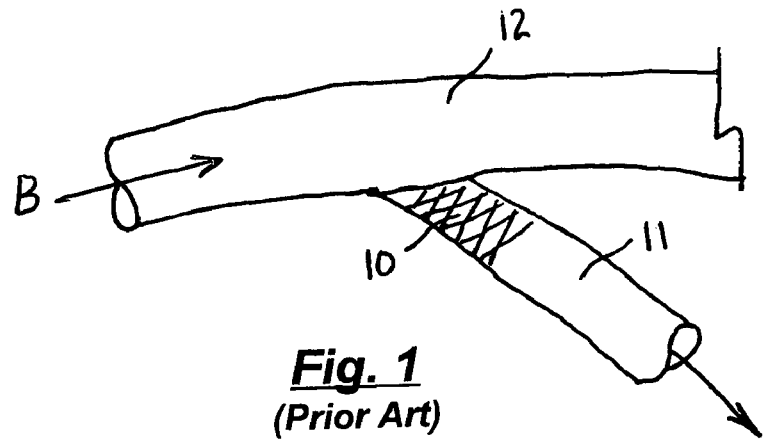
FIG. 1 shows a vessel in a coronary vascular system with a side branch that is totally occluded.
Figure 2:
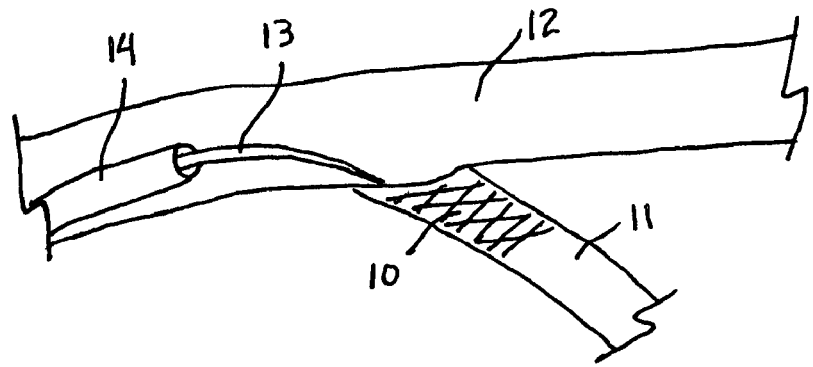
FIG. 2 shows a conventional technique used to perforate an occlusion with a stiff guide wire and a small catheter to position the guide wire at the occlusion.
Figure 3:
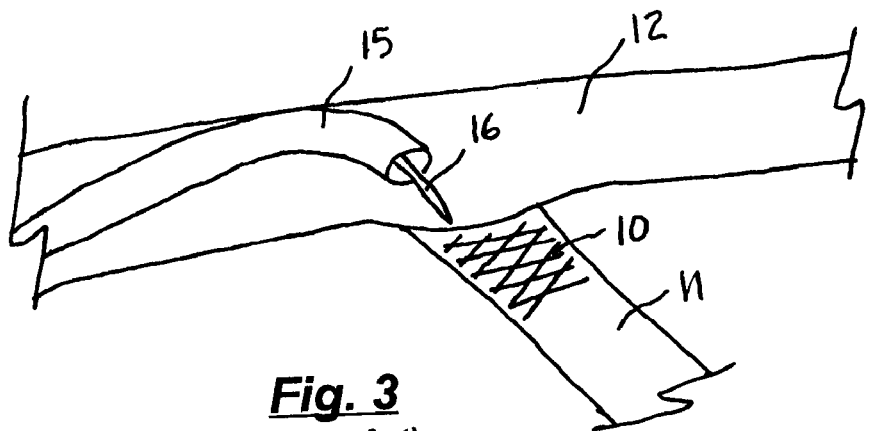
FIG. 3 shows a conventional technique that uses a curved catheter and/or curved catheter/guide wire combination to align the perforating guide wire with the angle of the side branch.
Figure 4:
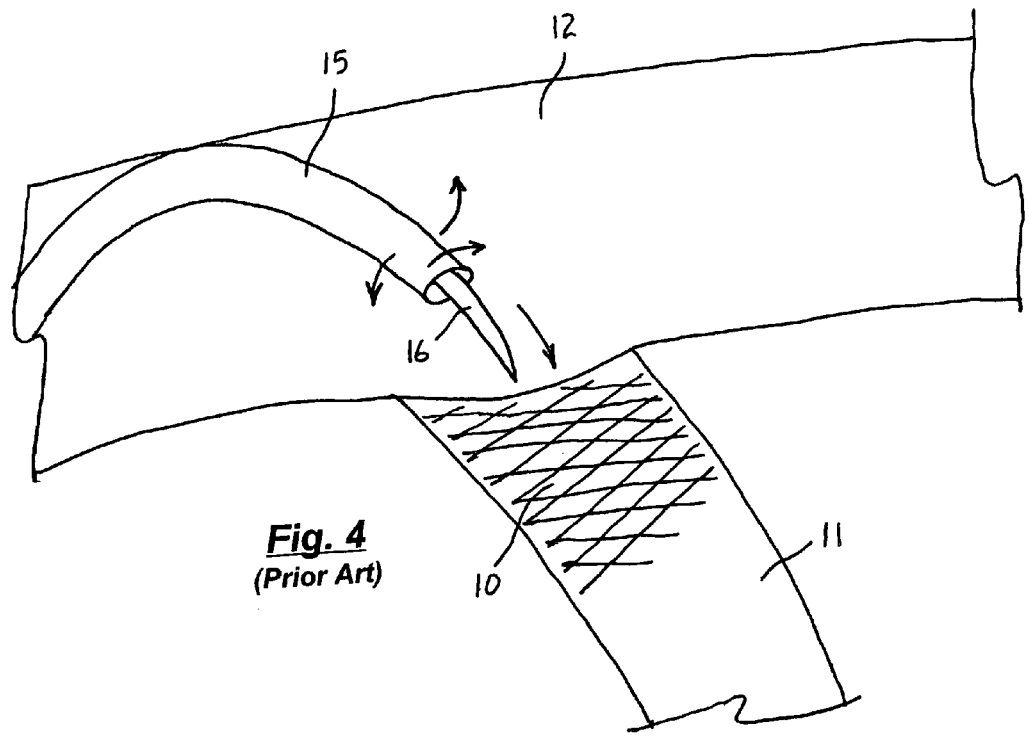
FIG. 4 illustrates the reactive forces on the catheter when the guide wire is pushed to perforate the occlusion using the conventional technique.
Figure 5:
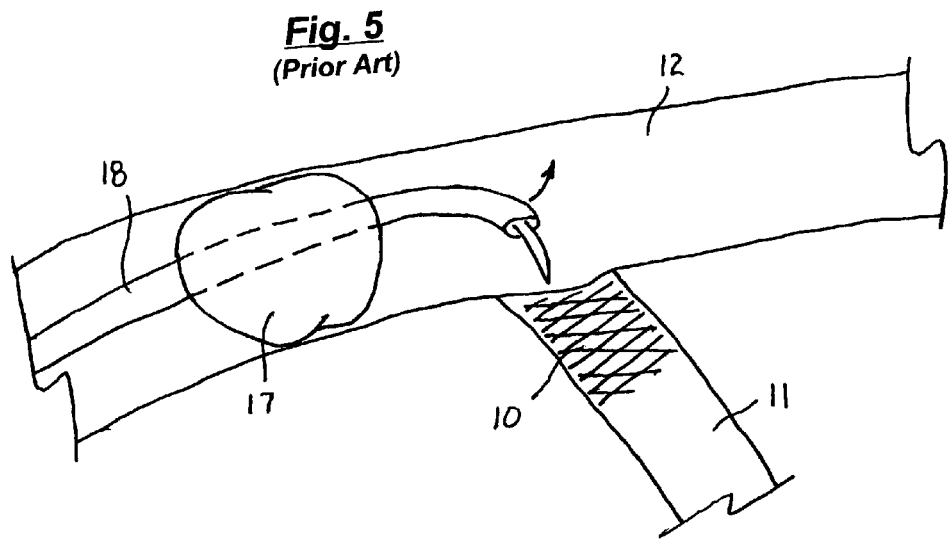
FIG. 5 shows a catheter with a balloon attached to help limit the reaction of the catheter as the guide wire is pushed into the occlusion.
Figure 6:
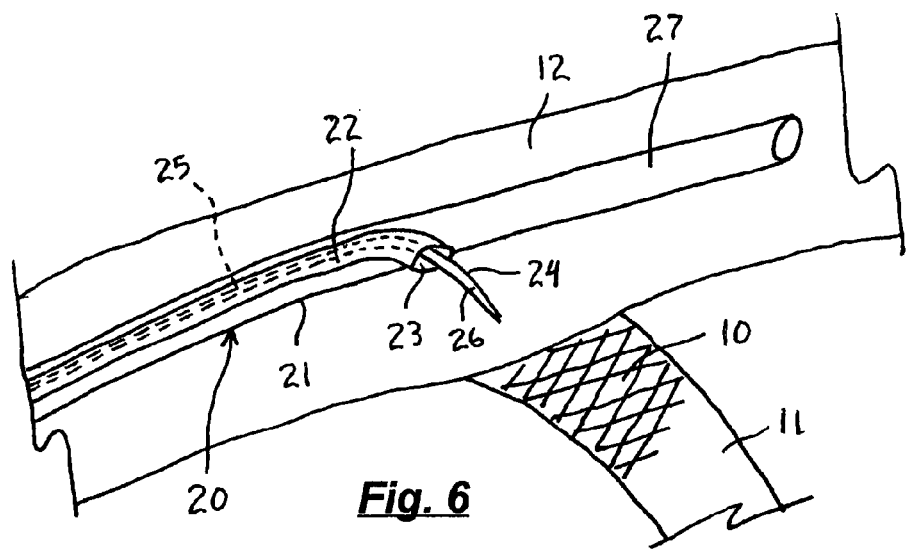
FIG. 6 shows a catheter according to an embodiment of the present invention having a side port through a sidewall for delivering a guide wire to a side branch occlusion in an artery.

FIG. 6 shows a catheter 20 having a sidewall 21 and an internal lumen 22. A side port 23 is formed through the sidewall 21 of the catheter 20. A perforating guide wire 24 is provided in the catheter 20 for accessing and treating a side branch occlusion 10 in an artery 12. The guide wire 24 has a proximal portion 25 within the internal lumen 22 of the catheter 20 and a distal portion 26 arranged to be movable out of the side port 23. The side port 23 is arranged to bend the guide wire 24 away from a longitudinal axis of the catheter 20 as the guide wire 24 passes through the side port 23. The guide wire 24 can thus be delivered through the side port 23 to the occlusion 10 in the side branch 11 of the artery 12.

In FIG. 6, a distal portion 27 of the catheter 20 extends for some distance past the side port 23 to add stability to the catheter 20 while the guide wire 24 is being delivered through the side port 23. The perforating guide wire 24 may be either straight or formed with a pre-curved tip at its distal portion 26. If a curved tip guide wire 24 is used, the guide wire 24 will be held straight within the lumen 22 of the catheter 20 until the distal portion 26 of the guide wire 24 exits through the side port 23. The length of the catheter 20 will help stabilize the catheter 20 as the curved guide wire 24 is pushed through the catheter 20. If a straight guide wire is used, the guide wire 24 must be flexible enough to deflect and bend as it enters the curvature contained within the catheter 20 to deflect the guide wire 24 out of the side port 23.

The catheter 20 with the side port 23 shown in FIG. 6 will torque with very little "whip" and allow for relatively easy positioning of the side port 23. The compressive force of the guide wire 24 necessary to deflect it through the side port 23 will result in a tensile loading on the catheter shaft that is fairly easy to restrain.

Figure 7:
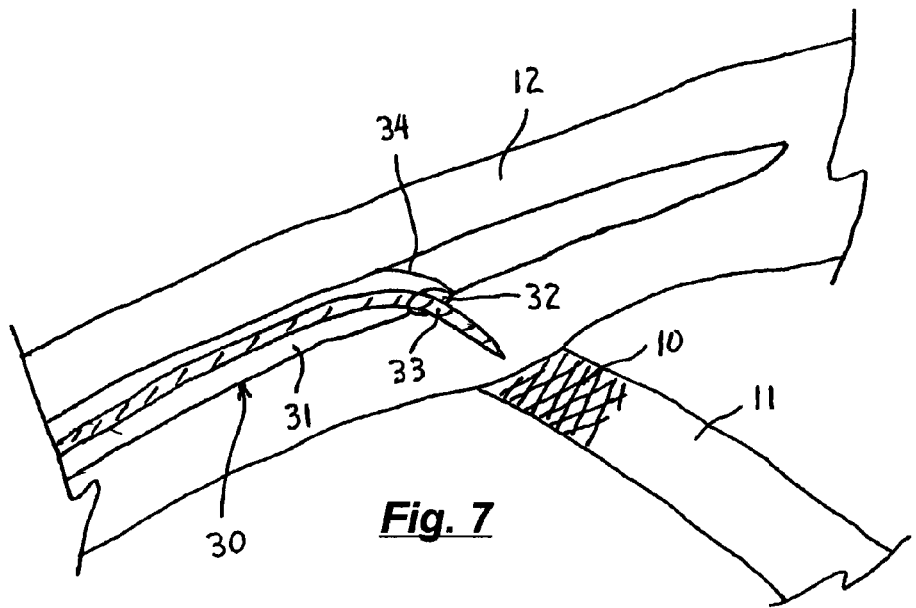
FIG. 7 shows another embodiment of the present invention in which the catheter contains a single lumen and side port through which the guide wire is passed.

FIG. 7 shows an embodiment of a catheter 30 in which the catheter contains a single lumen 31 and side port 32 through which the guide wire 33 is passed. The single lumen 31 truncates at its distal end 34 to the side port 32 to guide the guide wire 33 to the opening of the side port 32.

Figure 8:
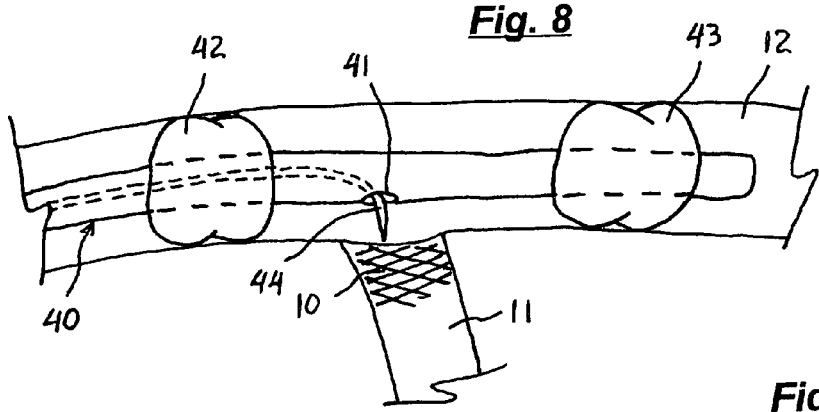
FIG. 8 shows another embodiment of the present invention in which support balloons are used to stabilize the catheter during usage.

FIG. 8 shows an embodiment of a catheter 40 with a side port 41 in which one or more support balloons 42, 43 are used to stabilize the catheter 40 during delivery of the guide wire 44 through the side port 41. A first balloon 42 can be positioned proximal of the side port 41, and a second balloon 43 can be positioned distal of the side port 41.

Figure 9:
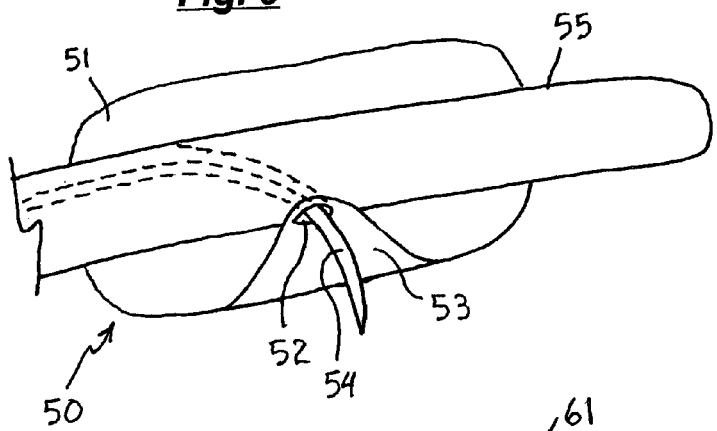
FIGS. 9 and 10 show another embodiment of the present invention in which a single support balloon is centered over the side port and attached to the catheter shaft at the proximal and distal ends of the balloon and around the side port.
Figure 10:
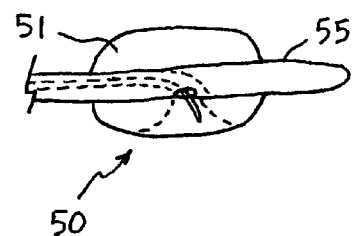

FIGS. 9 and 10 show an embodiment of a catheter 50 in which a single support balloon 51 surrounds the catheter 50 adjacent to the side port 52 and has a recess 53 in the support balloon 51 to allow delivery of the guide wire 54 through the side port 52. In this case, the balloon 51 can be centered over the side port 52 and attached to the outer sleeve 55 of the catheter 50 at the proximal and distal ends of the balloon 51 and around the side port 52.

Figure 11:
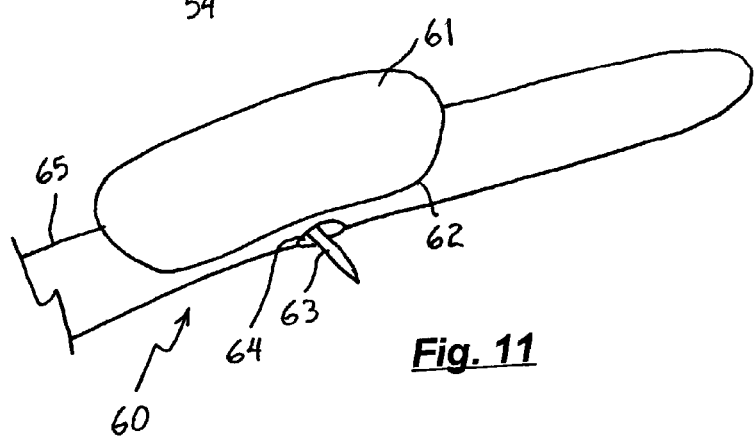
FIG. 11 shows another embodiment of the present invention in which a "hot dog bun"-shaped balloon is centered about the side port and attached to the catheter shaft.

FIG. 11 shows an embodiment of a catheter 60 in which a balloon 61 having a general shape of a hotdog bun is used for stabilizing the catheter 60. In this embodiment, the balloon 61 has an open side 62 for allowing delivery of the guide wire 63 through the side port 64. The balloon 61 can be centered about the side port 64 and attached to the outer sleeve 65 of the catheter 60 as shown.

FIG. 12 shows an embodiment of a catheter 70 in which two lumens 71, 72 are provided in the catheter. The first lumen 71 serves as the lumen for delivering the guide wire to the side port 73, and the second lumen 72 serves as a balloon inflation lumen for delivering gas or fluid to a balloon inflation port 74 for inflating the support balloon or balloons after insertion of the catheter 70 into a patient.

FIGS. 13 and 14 show an embodiment of a catheter 80 in which an insertion lumen 81 is provided for inserting the catheter 80 over a second guide wire 82 previously placed in the non-occluded portion of the artery 12. The second guide wire 82 can pass through the insertion lumen 81 for guiding the catheter 80 into position within a patient's body. As shown in FIG. 13, the insertion lumen 81 is open at both its distal and proximal ends 83, 84 and arranged so that the balloon and the balloon inflation port 85 and the side port 86 of the catheter 80 are located between the distal and proximal ends 83, 84. The insertion lumen 81 passes through the inflation lumen 87 of the catheter 80.

Figure 15:
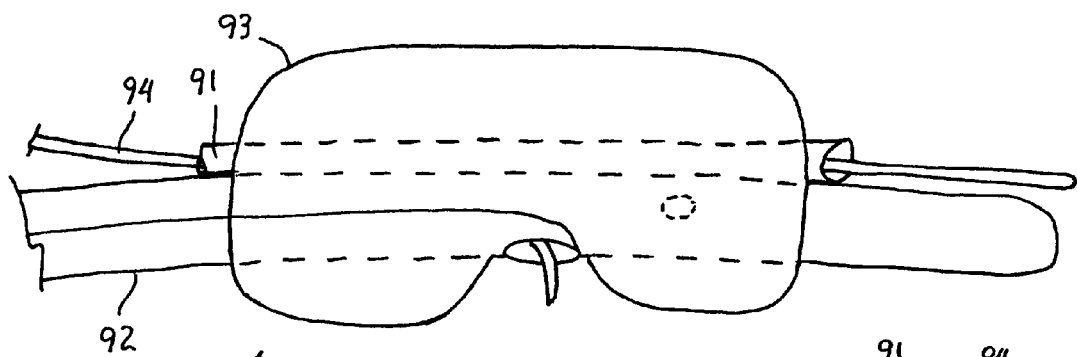
FIGS. 15 and 16 are side and end views of another embodiment of the present invention in which a guide wire lumen is provided on the exterior of the primary catheter with a support balloon.
Figure 16:
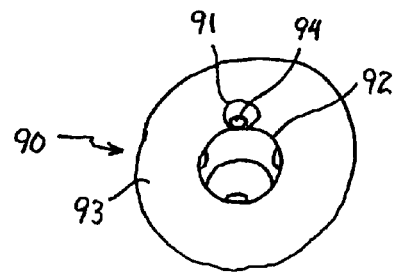
Figure 17:
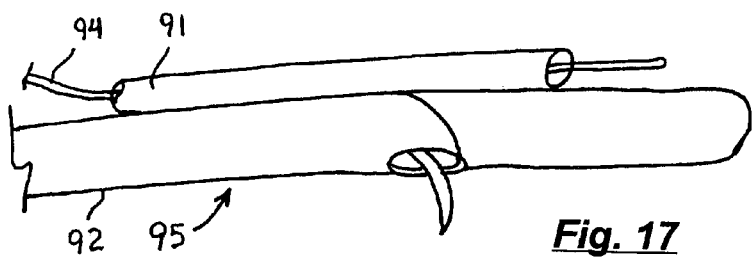
FIG. 17 shows another embodiment of the present invention in which a guide wire lumen is provided on the exterior of the primary catheter without a support balloon.

FIGS. 15 and 16 show an embodiment of a catheter 90 in which a tubular member 91 is provided on the exterior of the primary catheter 92. The tubular member 91 provides an insertion lumen for a second guide wire 94 used to guide the catheter 90 into position within a patient's body. In this embodiment, a support balloon 93 surrounds both the tubular member 91 and the primary catheter 92. FIG. 17 shows a similar embodiment of a catheter 95, except that no support balloon is used.

Figure 18:
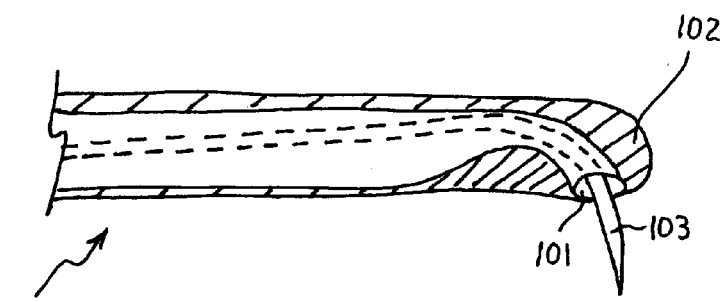
FIG. 18 shows another embodiment of the present invention in which no extension of the catheter extends past the side port, and a molded tip is provided to facilitate movement of the exiting guide wire.

FIG. 18 shows an embodiment of a catheter 100 in which no extension of the catheter extends past the side port 101. In this embodiment, a molded tip 102 is provided to facilitate movement of the exiting perforating guide wire 103.

FIGS. 19 to 21 show another embodiment of a catheter 110 in which the side port 111 is movable relative to the base portion 112 of the catheter 110 to change the angle $\alpha$ at which the guide wire 113 exits the catheter 110. In this embodiment, the base portion 112 of the catheter 110 has a molded internal guide 114 within its tip 115, and a movable portion 116 in which the side port 111 is formed. The base portion 112 and movable portion 116 are telescoping members that can be adjusted relative to one another. As the side port 111 on the movable portion 116 is positioned relative to the base portion 112, the angle $\alpha$ of the guide wire 113 exiting the catheter 110 will change. In other words, the movable portion 116 can be moved relative to the base portion 112 to adjust the angle $\alpha$ of the guide wire 113 exiting the catheter 110. The relative positions of the movable portion 116 and the base portion 112 can be adjusted during a surgical procedure using a push/pull wire or by applying a fluid pressure within a lumen 117 of the base portion 112. Support balloons and the like as described above can be incorporated into this embodiment as desired.

FIG. 22 show an embodiment of a catheter 120 in which telescoping sleeves 121, 122 are used to change the angle $\alpha$ at which the guide wire 113 exits the side port 111 of the catheter 110. The telescoping sleeves 121, 122 will provide a convenient means by which a surgeon can adjust the relative positions between the outer "movable" portion 121 and the inner "base" portion 122 of the catheter 120 from the proximal end of the catheter 120.

Figure 23:
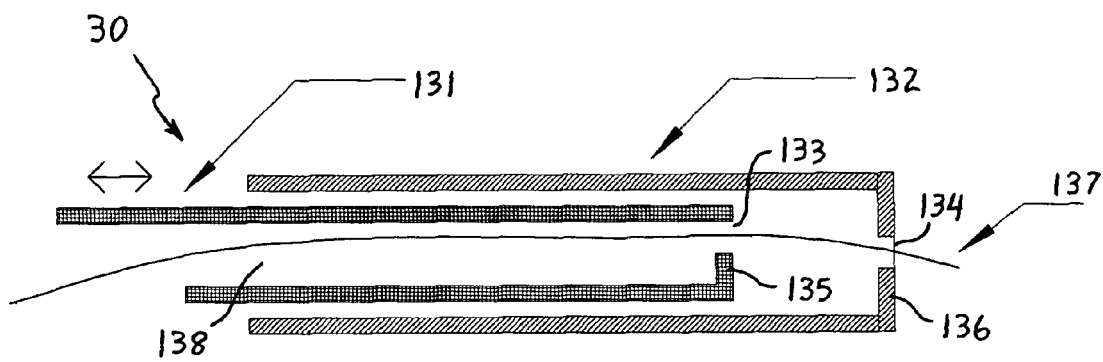
FIG. 23 shows another embodiment of the present invention in which telescoping inner and outer tubes having offset ports at their distal ends are used to change the angle at which the guide wire exits the catheter.
Figure 24:
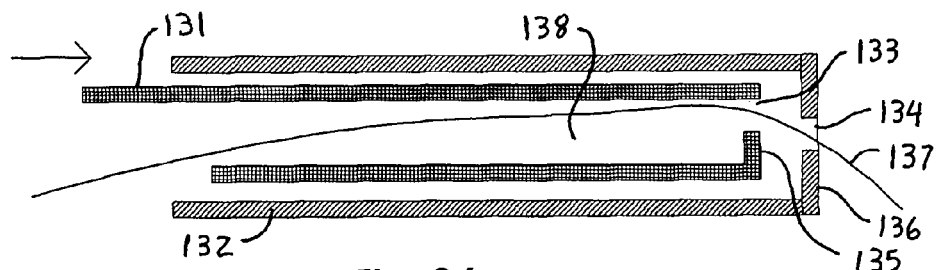
FIGS. 24 and 25 show the catheter of FIG. 23 with the inner tube at different positions relative to the outer tube to cause the guide wire to exit the catheter at different angles.
Figure 25:
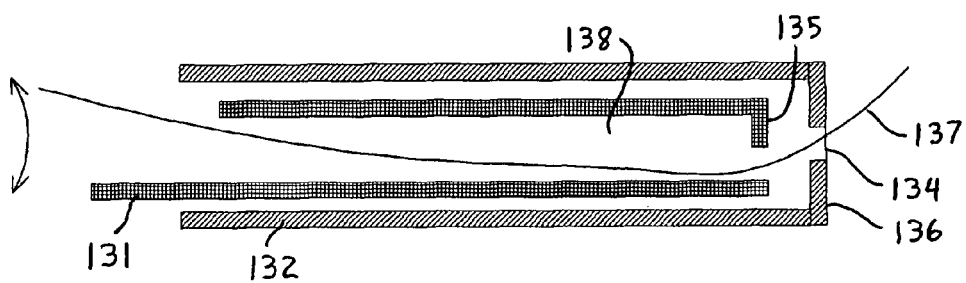

FIGS. 23 to 25 show another embodiment of a catheter 130 in which telescoping inner and outer tubes 131, 132 having offset ports 133, 134 at their distal ends 135, 136 are used to change the angle at which the guide wire 137 exits the catheter 130. The inner and outer tubes 131, 132 are arranged for rotational and/or telescoping movement relative to each other. For example, the inner tube 131 can be moved in a telescoping manner relative to the outer tube 132 from the position shown in FIG. 23 to the position shown in FIG. 24. Further, the inner tube 131 can be moved in a rotational manner relative to the outer tube 132 from the position shown in FIG. 24 to the position shown in FIG. 25.

Figure 26:
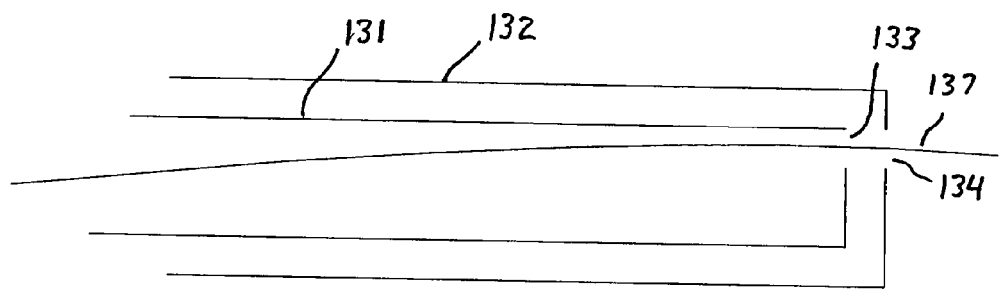
FIGS. 26 and 27 show another variation of the catheter of FIG. 23 in which the exit port of the outer telescoping tube is offset from the longitudinal axis of the catheter.
Figure 27:
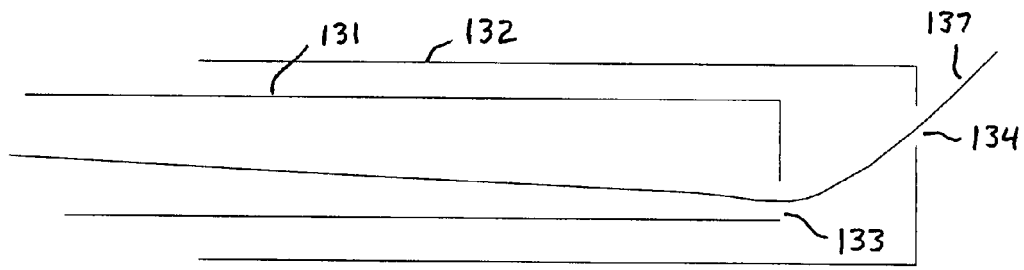

The inner tube 131 has an internal lumen 138 that leads to the first port 133 at the distal end 135 of the inner tube 131. The outer tube 132 has the second port 134 at the distal end 136 of the outer tube 132. In the embodiment shown in FIGS. 23 to 25, the first port 133 is offset from the longitudinal axis of the catheter 130, and the second port 134 is approximately concentric with the longitudinal axis. In the embodiment shown in FIGS. 26 and 27, both the first and second ports 133, 134 are offset from the longitudinal axis of the catheter. In both embodiments, the first and second ports 133, 134 are offset relative to each other so that relative movement between the inner and outer tubes 131, 132 will cause relative movement between the first and second ports 133, 134 to adjust an angle of the perforating guide wire 137 exiting the catheter.

In the catheter embodiments shown in FIGS. 23 to 27, the degree of deflection of the guide wire 137 can be increased or decreased by telescoping the tubes 131, 132, and/or by rotating one or both tubes 131, 132 to change the alignment of the first and second ports 133, 134. The catheter 130 can also be used in combination with an inflatable stabilizing balloon as described above in connection with the other embodiments disclosed herein.

Catheter devices according to various embodiments of the present invention have been described above. Methods of using these catheter devices to access a side branch 11 of an artery 12 will now be described.

The basic method includes a first step of providing a catheter 20 having a sidewall 21 and an internal lumen 22, a side port 23 formed through the sidewall 21, and a perforating guide wire 24 positioned within the internal lumen 22. A second step is to deploy the catheter 20 to a location with the side port 23 suitably aligned with a side branch 11 of an artery 12 to be accessed. A third step is to move the guide wire 24 through the side port 23 and into the side branch 11 of the artery 12.

In the catheter embodiments having a distal portion 27 that extends past the side port 23, the method will include the step of positioning the distal portion 27 on a distal side of the side branch 11 of the artery 12 to stabilize the catheter 20 while the guide wire 24 is being delivered through the side port 11.

In the catheter embodiments having one or more balloons 42, 43 attached to the catheter, the method may include the further step of inflating the balloon 42, 43 within the artery 12 to stabilize the catheter while the guide wire 44 is being delivered through the side port 41. As described above, a first balloon 42 can be positioned proximal of the side port 41 and a second balloon 43 can be positioned distal of the side port 41.

In the catheter embodiments having an insertion lumen 81, the method may include the further step of guiding the catheter within a patient's body over a second guide wire 82 that passes through the insertion lumen 81. As described above, the insertion lumen 81 has open distal and proximal ends 83, 84 and is arranged so that the side port 86 of the catheter is located between the distal and proximal ends 83, 84.

In the catheter embodiments having a base portion 112 and a movable portion 116 with the side port 111 formed in the movable portion 116, the method may include the further step of moving the movable portion 116 relative to the base portion 112 to adjust an angle $\alpha$ of the guide wire 113 exiting the catheter.

While the invention has been described in connection with specific embodiments thereof, it is to be understood that this is by way of illustration and not of limitation, and the scope of the appended claims should be construed as broadly as the prior art will permit.

What is claimed is:

1. A method of accessing a side branch in an artery, comprising the steps of:
   providing a catheter having an inner tube and an outer tube arranged for rotational and/or telescoping movement relative to each other, said inner tube having an internal lumen and a first port at a distal end of the inner tube, said outer tube having a second port distal of said first port, said first port being offset from said second port relative to a longitudinal axis of the catheter, and a perforating guide wire extending through said internal lumen and exiting from the inner and outer tubes through the first and second offset ports, respectively, said perforating guide wire being engaged by said second port; and
   moving said outer tube relative to said inner tube to cause relative movement between said first and second ports to change the relative positions of said first and second ports to adjust an angle of the perforating guide wire exiting the catheter.

2. The method according to claim 1, wherein said second port is located at a distal end of the outer tube.

3. The method according to claim 1, wherein said inner tube and said outer tube are arranged for rotational movement relative to each other, and said step of moving said outer tube relative to said inner tube comprises rotating said outer tube relative to said inner tube.

4. The method according to claim 1, wherein said inner tube and said outer tube are arranged for telescoping movement relative to each other, and said step of moving said outer tube relative to said inner tube comprises telescoping said outer tube relative to said inner tube.

* * * * *